United States Patent
Hessel et al.

[19]

[11] Patent Number: 6,017,355
[45] Date of Patent: Jan. 25, 2000

[54] INTERCUTANEOUS IMPLANT DEVICE

[75] Inventors: Lasse Leif Hessel; Jorgen Scherning Lundsgaard; Carl Zimmermann-Neilsen; John Engell, all of Svendborg; Jesper Malling, Odense M.; David Morgan Thomas, Stenstrup, all of Denmark

[73] Assignee: Bio TAP A/S, Svendborg, Denmark

[21] Appl. No.: 09/103,919

[22] Filed: Jun. 24, 1998

[30] Foreign Application Priority Data

Jun. 25, 1997 [DK] Denmark ................................. 0749/97

[51] Int. Cl.[7] .................................................. A61B 17/14
[52] U.S. Cl. ......................... 606/184; 606/186; 604/174; 604/175
[58] Field of Search ..................... 606/109, 184; 604/174, 175, 176, 177, 180; 623/11, 12; 128/283

[56] References Cited

U.S. PATENT DOCUMENTS

| | | | |
|---|---|---|---|
| 4,183,357 | 1/1980 | Bentley et al. | 128/283 |
| 4,265,244 | 5/1981 | Hill | 128/283 |
| 4,534,761 | 8/1985 | Raible | 604/175 |
| 5,234,408 | 8/1993 | Griffith | 604/93 |
| 5,242,415 | 9/1993 | Kantrowitz et al. | 604/175 |
| 5,290,251 | 3/1994 | Griffith | 604/174 |

FOREIGN PATENT DOCUMENTS

| | | | |
|---|---|---|---|
| 2019219 | 10/1979 | United Kingdom | 604/174 |
| 2 056 282 | 12/1979 | United Kingdom . | |

*Primary Examiner*—Michael Buiz
*Assistant Examiner*—Uen Ngo
*Attorney, Agent, or Firm*—Law Offices of Jane Massey Licata

[57] ABSTRACT

Intercutaneous implant devices useful in intraluminal and extraluminal procedures for externalization of vessels are provided which have a hollow cylinder with an upper and lower end and an interior and exterior surface, said hollow cylinder having a central aperture which is greater in diameter than the exterior expanse of the access site and a length which provides for adequate annular separation of the externalized vessel at the exterior and interior surface of the implant to ensure adequate blood supply to the vessel; a flange extending from the upper end of the hollow cylinder which provides a platform onto which is attached a termination device; and a plane contacting surface extending from the lower end of the hollow cylinder which provides a means for fixation of the implant to the patient.

8 Claims, 3 Drawing Sheets

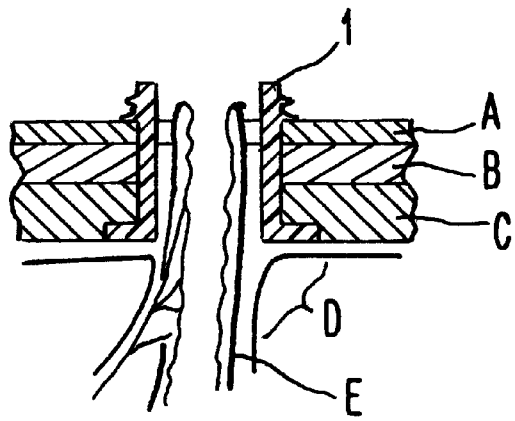
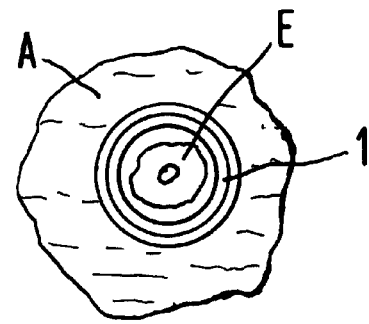
Fig. 3A　　Fig. 3B
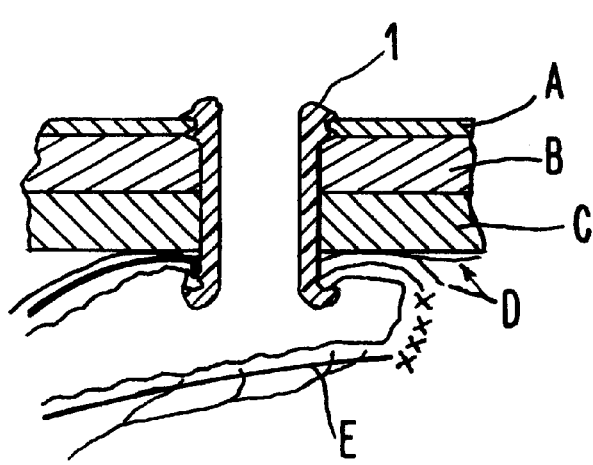
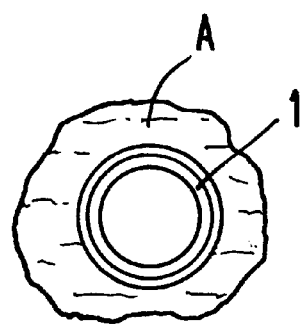
Fig. 4A　　Fig. 4B

INTERCUTANEOUS IMPLANT DEVICE

INTRODUCTION

This application is a continuation-in-part of Danish Provisional Application No. DK-0749/97, filed on Jun. 26, 1997.

FIELD OF THE INVENTION

The present invention relates to bio-compatible polymeric implant devices for use as temporary or chronic intercutaneous conduit means for externalizing internal vessels and/or organs. The implant is constructed so as to provide a platform, onto which can be mounted or attached a variety of detachable termination devices such as caps, removable pouches and tubes. The implant comprises a hollow cylinder or barrel terminated at its upper end by a flange and at the bottom end by a plane contacting surface. In a preferred embodiment, the implant further comprises a plurality of textile fixtures or a textile ring extending perpendicularly from the plane contacting surface and/or hollow cylinder which can be fixed to the subcutis or muscle fascia to create a fibrous plate which fastens and stabilizes the implant thereby avoiding any tilting of the implant during manipulation of any termination devices. Implants of the present invention are useful in both extraluminal and intraluminal procedures.

DESCRIPTION OF THE PRIOR ART

There are numerous medical conditions which require a surgical procedure to externalize an internal body vessel such as, but not limited to, the colon, small intestine, ureter or bladder. For example, patients undergoing partial or total surgical removal of the colon generally require an enterostomy. Ileostomy is a surgical procedure wherein the small intestine is opened and drained or brought through the abdominal wall. Typically, enterostomies are accomplished by severing the vessel which is to be externalized and then suturing the wall of the vessel to an opening which has been formed on the surface of the body. The opening is normally located in the abdominal area. In time, the wall of the vessel and the dermis of skin surrounding the opening will grow together to permanently secure the vessel to the body surface. After the operation has healed, a container is typically attached to the surface of the skin to collect excrements which are discharged from the vessel. However, due to the acidic and enzymatic nature of fecal matter, ulcers often develop on the skin surrounding the point of externalization. Accordingly, various transcutaneous implant devices have been developed for use in enterostomies and other similar procedures which prevent matter being discharged from the externalized vessel or organ from contacting the skin.

For example, U.S. Pat. Nos. 5,234,408 and 5,290,251 disclose a tissue bondable cystotomy tube which overcomes problems with urinary leakage associated with suprapubic cystostomy and percutaneous cystostomy. This cystostomy tube comprises a subcutaneous hollow cylinder having an upper and lower end, a planar disc extending radially from the lower end of the subcutaneous hollow cylinder used for positioning and alignment of the subcutaneous hollow cylinder with the bladder membrane and a transcutaneous hollow cylinder also having a lower and upper end wherein the lower end of the transcutaneous hollow cylinder is slidably received into the upper end of the subcutaneous hollow cylinder. The exterior surface of both cylinders and the planer disc are coated with a material suitable for bonding with biological tissue. In a preferred embodiment, this cystostomy tube further comprises a stabilizing slipover disc sleeve centrally located on the exterior surface of the subcutaneous hollow cylinder which is also coated with a material suitable for bonding with biological tissue and which provides a means for stabilizing and aligning the cystostomy tube in the patient. This cystostomy tube is surgically implanted in phases over a period of several weeks or months into the patient. The first phase involves implantation of the subcutaneous hollow cylinder with a removable plug in the region of the bladder membrane. The subcutaneous hollow cylinder and plug are allowed to remain in the patient for a sufficient period of time for tissue bonding to occur, i.e., several weeks or months. After this tissue bonding has occurred, a circular portion of skin and subcutaneous fat which forms above the subcutaneous hollow cylinder is excised. The plug is removed from the subcutaneous hollow cylinder and the lower end of the transcutaneous hollow cylinder is slidably inserted into the subcutaneous hollow cylinder. The two cylinders are then allowed to remain in the patient for a sufficient period of time for tissue bonding to occur to the transcutaneous hollow cylinder. The cystostomy tube is then activated by inserting a trocar into the transcutaneous hollow cylinder and puncturing the internal bladder membrane. A cap is then affixed to the upper end of the transcutaneous hollow cylinder.

U.S. Pat. No. 4,183,357 discloses a chronic transcutaneous implant assembly for enterostomies. The implant device contains a cylindrical or barrel portion which is integrally linked to a flange portion. The barrel portion has a plurality of apertures or limited areas of porous material which enable the ingrowth of the tissue of the externalized vessel through the implant into the dermis thereby forming a vascularized connection for the vessel and preventing necrosis. The flange portion also has a plurality of apertures or limited areas of porous material which enable the ingrowth of vascularized dermis tissue to form a biological anchor for the implant. It is preferred that the implant device be combined with a disposable, detachable bag member which functions to receive excrements exiting the externalized vessel.

U.S. Pat. No. 4,534,761 (Raible et al.) also discloses an implant device which includes a passageway extending through the device and an anchor means which preferably includes a plurality of apertures for establishing a biological anchor. In one embodiment, the implant device also includes an annular rim which forms an annular recess between the annular rim and the anchor means. Grafting mesh is also positioned annularly about at least a portion of the exterior of the implant device. The grafting mesh is spaced apart from the implant device by means of a spacer in order to allow tissue ingrowth between the implant device and the grafting mesh.

However, experience in these surgeries indicates that interference with the blood supply to the externalized vessel leads to complications, particularly loss of viability. This necessitates reformation of the enterostomy with viable vessel. Direct mucocutaneous contact with the implant, which occurs in the implant devices described above, reduces the blood supply to the adjacent tissue via the mesentery thereby causing necrosis. It is also difficult to maintain the biocompatible bond to the implant, due to excessive local stress at the interface between tissue and implant.

Another problem arises due to the passage of intestinal content through the implant aperture where peristaltic activity is absent, e.g., pathogenesis during Hirschprung's type syndrome. When passage of intestinal fluids occurs due to increase of the intraluminal pressure in the colon, then problems requiring irrigation can arise.

In the present invention, an improved implant for the general purpose of externalizing vessels is provided which overcomes these disadvantages.

SUMMARY OF THE INVENTION

An object of the present invention is to provide an intercutaneous implant device useful in intraluminal and extraluminal procedures for externalization of vessels which comprises a hollow cylinder having an upper and lower end and an interior and exterior surface, said hollow cylinder having a central aperture which is greater in diameter than the exterior expanse of the access site and a length which provides for adequate annular separation of the externalized vessel at the exterior and interior surface of the implant to ensure adequate blood supply to the vessel; a flange extending from the upper end of the hollow cylinder which provides a platform onto which is attached a termination device; and a plane contacting surface extending from the lower end of the hollow cylinder which provides a means for fixation of the implant to the patient. In a preferred embodiment, the implant further comprises a textile ring or fixtures extending perpendicularly from the plane contacting surface and/or hollow cylinder of the implant which can be sutured into the muscle for added support.

BRIEF DESCRIPTION OF THE DRAWINGS

FIG. 3A shows a cross-sectional side view of the implant in situ in a extraluminal procedure wherein the cutis is designated by A; the subcutis is designated by B; the fascia and muscle are designated by C; the peritoneum is designated by D; and the colon with supplying vascularization is designated by E.

FIG. 3B show the external view of the implant in this extraluminal procedure.

FIG. 4A shows a cross-sectional side view of the implant in situ in an intraluminal procedure wherein the cutis is designated by A; the subcutis is designated by B; the fascia and muscle are designated by C; the peritoneum is designated by D; and the colon with supplying vascularization is designated by E. The intraluminal procedure involves introduction of the implant device through the abdominal wall and into the intestinal lumen, such as the colon sigmoideum.

FIG. 4B shows the external view of the implant in this intraluminal procedure.

DETAILED DESCRIPTION OF THE INVENTION

In the present invention a biocompatible polymeric implant is provided for use in externalizing vessels. It is intended to be applied in connection with access to body tissue and access or externalization of internal vessels, such as intestines, bladder, etc., or any other amenable organ in the body. The implant is constructed so as to provide a platform onto which can be mounted or attached a variety of detachable termination devices, such as caps, removal bags, tubes, etc. During application, the implant penetrates through the epithelium, dermis and subcutaneous adipose tissue to rest on the deep facia below, to which it may be secured by suture. When used in enterostomy or colostomy, the implant device of the present invention allows protection of the abdominal skin from the adverse effects of contact with excrement, and also avoids the use of adhesives in order to attach disposable, detachable collection bags directly onto the skin.

Figure 1:
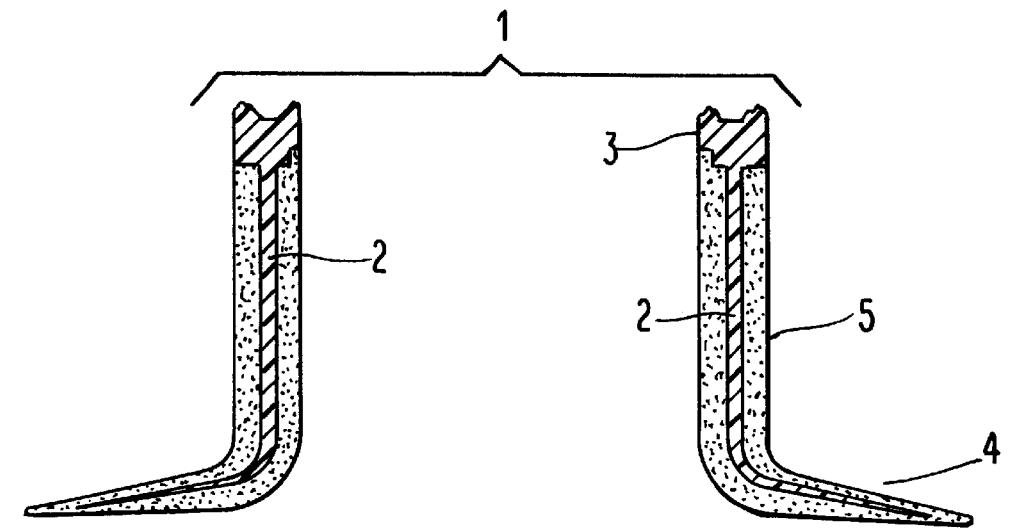
FIG. 1 shows a cross-sectional side view of an implant of the present invention.

In simplest form, as depicted in FIG. 1, the implant 1 comprises a hollow cylinder 2 terminated at its upper end by a flange 3 and at the bottom end by a plane contacting surface 4. The flange 3 of the implant 1 provides a platform, onto which can be mounted or attached a variety of detachable termination devices such as caps, removable pouches and tubes while the plane contacting surface 4 provides a means 5 for fixation of the implant to the patient. For example, in one embodiment, the plane contacting surface 4 is perforated to facilitate suturing of the implant to the muscle fascia.

The implant material is selected from the list of biocompatible materials approved by the U.S. Food and Drug Administration (FDA). The preferred material is a moldable polyester thermoplastic which has been found on the list of approved materials.

In one embodiment, to be used for implanting in the usual manner where established conventional surgical procedures apply, the hollow cylinder 2 of the implant 1 has a non-profiled portion which is covered with a textile surface layer 5 comprised of a porous polymer such as, but not limited to, DACRON mesh, PROLENE net, VICRYL net, or SURGIPRO mesh, for integration of the implant 1 between the external skin tissue and the internal vessel and/or organ. This covering provides for rapid vascularization and tissue ingrowth around the implant thereby assuring stability.

It is also very important to maintain blood supply to the tissues in contact with the implant. Accordingly, in the present invention, the implant 1 is removed from the access site by having a central aperture to its hollow cylinder 2 which is considerably greater than the exterior expanse of the access site. Further, subsequent surgeries may require access to the vessel which may be manipulated via the open aperture in the hollow cylinder of the implant. Accordingly, the size of the central aperture must be adequate to enable the manipulations required and is determined by the diameter of the enclosed stoma. For example, for colostomies, the diameter of the central aperture is the expected diameter of the outer skin surface of the externalized vessel and ranges from approximately 15 mm to 55 mm. However, as will be obvious to those of skill in the art upon this disclosure, the size of the central aperture of the hollow cylinder range is selected to provide for adequate control of interference and compatibility and is dependent upon the vessel being accessed.

The extent of the annulus separating the externalized organ boundary at the exterior and the internal surface of the implant must be sufficient to ensure adequate blood supply to the vessel. Typically, an annular separation of 5 to 25 mm from the externalized vessel is required. However, this may vary in accordance with the amount and/or thickness of adipose tissue of the patient. Adipose tissue thickness normally varies between 5 and 40 mm. Thus, the length of the hollow cylinder of the implant must be adjusted accordingly to provide for adequate annular separation of 5 to 25 mm.

Figure 2A:
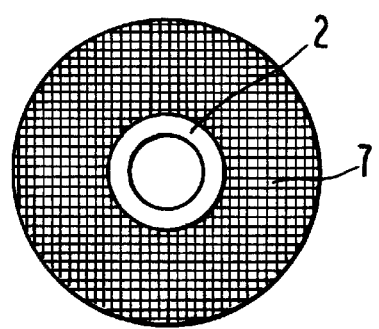
FIG. 2A shows a top view of a preferred embodiment of an implant of the present invention which depicts a textile ring extending perpendicularly from the hollow cylinder of the implant.
Figure 2B:
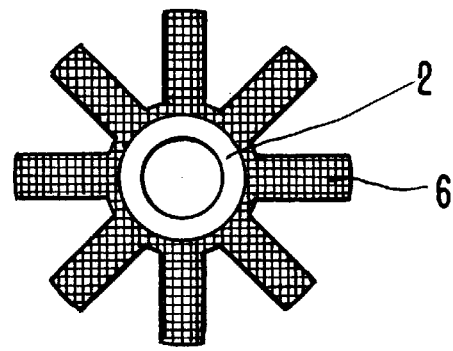
FIG. 2B shows a top view of a preferred embodiment of an implant which depicts textile fixtures extending perpendicularly from the hollow cylinder of the implant.

For example, in enterostomy or colostomy there must be adequate space for a portion of the mesentery or mesocolon to be carried up to the surface; otherwise, the externalized vessel will be likely to lose viability. The use of an implant in this way serves to provide a remote support to the accessed organ with a minimum of interaction with its function. The function of the implant is, therefore, to act as a support and at the same time, offer a platform for mounting various accessories, such as detachable bags, tubes, instrumentation, terminators and the like. Thus, in a preferred embodiment as depicted in FIG. 2a and 2b, the implant 1 further comprises a plurality of textile fixtures or fingers 6 (depicted in FIG. 2b) or a textile ring 7 (depicted in FIG. 2a) extending perpendicularly from the plane contacting surface of the implant which can be sutured into the muscle for added support. More preferably, the implant further comprises a plurality of textile rings 8 extending from the hollow cylinder 2 of the implant 1. It is preferred that the textile rings of finger be comprised of a porous polymer such as, but not limited to, DACRON, PROLENE net, VICRYL net, or SURGIPRO mesh. In this embodiment, the implant 1 is fixed to the subcutis or muscle fascia to create a fibrous plate which fastens and stabilizes the implant thereby preventing tilting of the implant 1 upon manipulation of the detachable termination device at the flange 3. By using this embodiment, and in particular the implant 1 wherein textile fixtures or fingers 6 or multiple layers of textile 8 extend from the plane contacting surface 4, optimal supply of blood to the tissue involved is maintained and vitality is improved for the normal tissue surrounding the stoma aperture.

Accordingly, the present invention provides a useful implant for permanent access to a vessel or organ such as may be required, for example, in a permanent colostomy, sigmoidostomy or transverse colostomy. Permanent colostomy (sigmoidostomy) using the implant of the present invention requires prior establishment of a relieving transverse stoma until the implant has been integrated and the associated wound healed. Further, to prevent Hirschprung's type syndrome at the constricting exit, especially for sigmoidostomy, the hollow cylinder 2 of the implant 1 is designed to convey peristalsis into the constriction formed by the implant. Hirschprung's type syndrome arises due to a loss of peristalsis in the bowel. Hirschprung's disease is actually caused by an absence of nerve cells in the wall of the bowel. Collections of nerve cells, called ganglia, control the coordinated relaxation of the bowel wall that is necessary for bowel contents to advance. Thus, in Hirschprung's disease, the portion of the bowel without ganglia cannot relax and thus remains collapsed so that stools cannot pass. A similar phenomena occurs with traditional implants which are not capable of peristalsis. However, material flow due to peristalsis can be assisted by appropriate design. When the flow length of an implant is large, considerable resistance to flow can arise which is similar conceptually to Hirschprung's type syndrome. The rise in abdominal pressure needed to overcome the flow resistance indicates that at least for extraluminal uses as depicted in FIG. 3, a flexible pipe capable of responding to peristaltic waves is more amenable. Thus, in one embodiment of the instant invention, the inner surface of the hollow cylinder 2 is smooth but the wall is flexible and capable of changing diameter significantly upon extension and distension of the cecum. In this embodiment, it is preferred that the hollow cylinder comprise an elastomeric tube with double spiral cord reinforcements.

In extraluminal procedures such as permanent colostomy prior establishment of a relieving transverse stoma until the implant has been integrated and the associated wound healed is required. In this procedure, the closed proximal sigmoideum is drawn through the abdominal incision and a normal colostomy operation is performed and concluded. Subsequently, after healing, a circular incision is made around the stoma down to the muscle fascia. The implant is then introduced around the stoma, and the plane contacting surface of the implant is sutured to the fascia. The upper flange is sutured to the dermis and, where used, the fingers of the textile material or textile ring are secured to the surrounding tissues.

Implants of the present invention are also useful in intraluminal procedures as depicted in FIG. 4. When carrying out intraluminal procedures, it is preferred that the implant be rigid to avoid collapse due to abdominal pressure. In intraluminal procedures, a side opening in the tenia is made on the terminated proximal sigmoideum and a hole is prepared with purse string sutures. The implant is introduced via the colostomy aperture in the abdominal wall and fitted into the prepared aperture in the sigmoideum. The purse string suture is secured and the sigmoideum wall is brought into contact and attached to the parietal peritoneum surrounding the exterior surface of the implant. The flange at the upper end of the hollow cylinder of the implant is sutured to the surrounding dermis.

Another object of the implant of the present invention is facilitation of implantation. Removal of possible interaction offers an opportunity for specializing on the support function described above, without unnecessarily complicating the operation. This means that access and implantation can be part of a two stage process in which each stage can be carried out in a sequential manner as separate, distinct steps.

Figure 5:
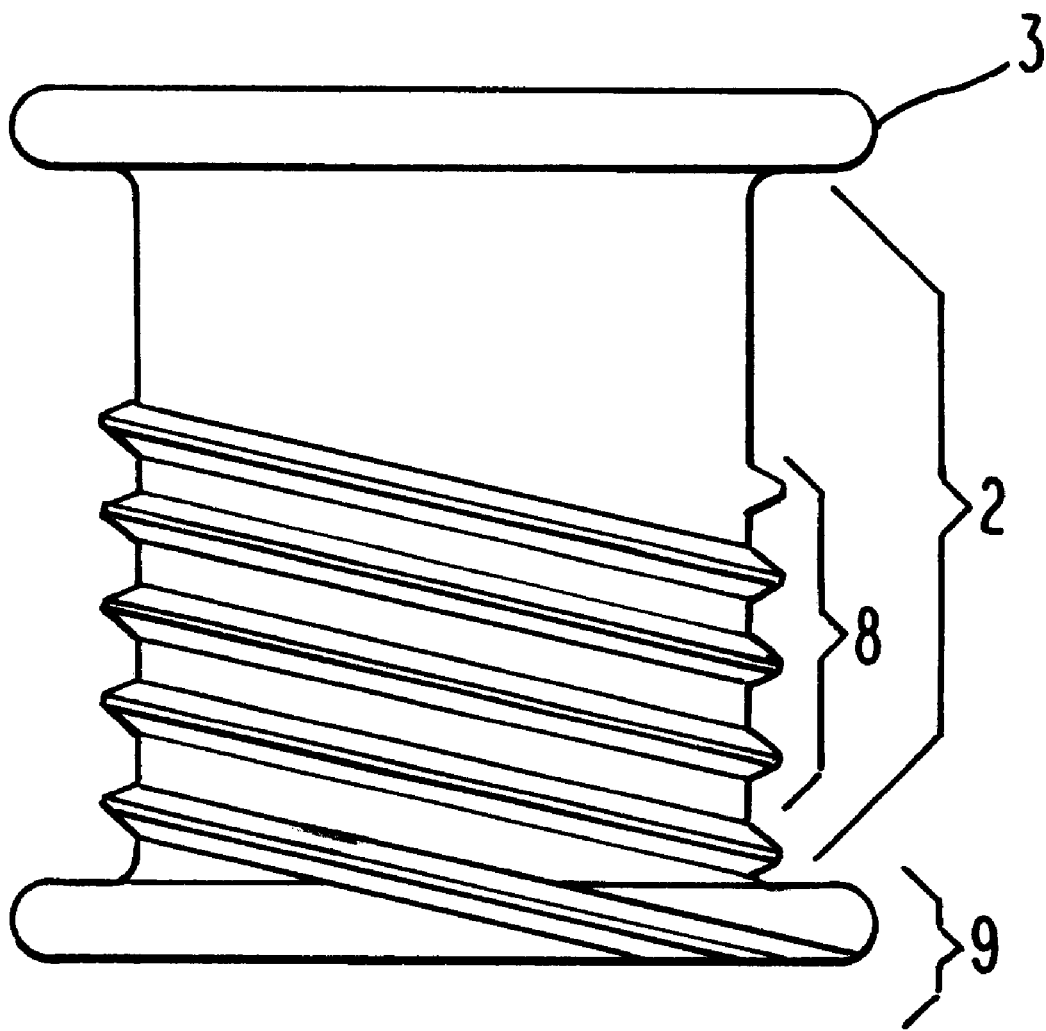
FIG. 5 shows a side view of an embodiment of an implant wherein the hollow cylinder is formed as a helical screw and the plane contacting surface is formed by a plurality of cutting edges which terminate as concurrent threads of the helical screw to enable penetration of the cutaneous tissue on axial rotation of the implant.

The step of implantation can then be simplified, facilitated and made more reliable. In an embodiment which exploits these possibilities, a simple implantation may be carried out by using a simple self-incising screw technique. The hollow cylinder 2 may be formed as a helical screw 8. In this embodiment, as depicted in FIG. 5, the plane contacting surface is formed by a plurality of cutting edges 9 which terminate as concurrent threads of the helical screw. The purpose of the cutting edges 9 is to enable penetration of the cutaneous tissue on axial rotation of the implant. In this embodiment, it is preferred that the upper portion of the hollow cylinder 2 including the flange 3 be covered with a porous material, for example, DACRON velour, which enables and encourages tissue ingrowth.

The implant may conveniently be introduced prior to or following access surgery, by applying vertical pressure on the top surface of the hollow cylinder 2, while rotating the hollow cylinder 2 to the angle required to give the calculated penetration depth. The appliance may be utilized in post-operative retro-fitting, where complications arising from the use of conventional termination devices require alternative measures which address the disadvantages. The screw pitch may be varied in order to give optimal penetration efficiency at a reasonable torque so that fitting the implant does little damage to the tissue in the surrounding area.

What is claimed is:

1. An intercutaneous implant device for externalization of vessels comprising:

(a) a hollow cylinder having an upper and lower end and an interior and exterior surface, said hollow cylinder having a central aperture which is greater in diameter than the exterior expanse of an access site thereby providing a space between the access site and the central aperture and a length which provides for adequate annular separation of an externalized vessel at the exterior and interior surface of the implant to ensure adequate blood supply to the vessel and to the adjacent tissue;

(b) a flange extending from the upper end of the hollow cylinder which provides a platform onto which is attached a termination device; and (c) a plane contacting surface extending from the lower end of the hollow cylinder which provides a means for fixation of the implant to the patient.

2. The intercutaneous implant device of claim 1 wherein the exterior surface of the hollow cylinder is covered with a textile surface layer comprised of a porous polymer.

3. The intercutaneous implant device of claim 1 further comprising a textile ring or a plurality of textile fixtures extending perpendicularly from the plane contacting surface of the implant.

4. The intercutaneous implant device of claim 3 further comprising a plurality of textile rings extending perpendicularly from the hollow cylinder of the implant.

5. The intercutaneous implant device of claim 1 wherein the hollow cylinder is rigid.

6. The intercutaneous implant device of claim 1 wherein the hollow cylinder is flexible and capable of changing diameter upon extension and distension of the vessel.

7. The intercutaneous implant device of claim 1 wherein the hollow cylinder is formed as a helical screw and the plane contacting surface is formed by a plurality of cutting edges which terminate as concurrent threads of the helical screw.

8. The implant device of claim 1 wherein the hollow cylinder is formed with a helical screw and the plane contacting surface is formed by a plurality of cutting edges which terminate in concurrent threads of said helical screw.

* * * * *